(12) United States Patent
Freers et al.

(10) Patent No.: US 9,918,942 B2
(45) Date of Patent: Mar. 20, 2018

(54) MICROSPHERES

(71) Applicant: Grain Processing Corporation, Muscatine, IA (US)

(72) Inventors: Susan Freers, Muscatine, IA (US); Carrie Shipley, Muscatine, IA (US); Brian Jensen, Muscatine, IA (US); Shawn Engels, Muscatine, IA (US)

(73) Assignee: Grain Processing Corporation, Muscatine, IA (US)

( * ) Notice: Subject to any disclaimer, the term of this patent is extended or adjusted under 35 U.S.C. 154(b) by 85 days.

(21) Appl. No.: 13/623,591

(22) Filed: Sep. 20, 2012

(65) Prior Publication Data

US 2013/0071479 A1     Mar. 21, 2013

Related U.S. Application Data

(60) Provisional application No. 61/536,919, filed on Sep. 20, 2011.

(51) Int. Cl.
    *A61K 9/14*      (2006.01)
    *B05D 5/00*      (2006.01)
     (Continued)

(52) U.S. Cl.
     CPC .......... *A61K 9/5078* (2013.01); *A61K 9/1652* (2013.01); *A61K 9/5036* (2013.01); *Y10T 428/2989* (2015.01)

(58) Field of Classification Search
None
See application file for complete search history.

(56) References Cited

U.S. PATENT DOCUMENTS 4,568,560 A * 2/1986 Schobel .................. 424/401
4,680,189 A     7/1987 Schumacher et al.
(Continued)

FOREIGN PATENT DOCUMENTS

CN     101317666 A1     12/2008
EP        0252881 A1     1/1988
(Continued)

OTHER PUBLICATIONS

English Translation of WO 2004/084863 A1.*
(Continued)

*Primary Examiner* — Bethany P Barham
*Assistant Examiner* — Dominic Lazaro
(74) *Attorney, Agent, or Firm* — Fitch, Even, Tabin & Flannery LLP

(57) ABSTRACT

The disclosure relates to substantially uniform, high density microspheres and methods of making the microspheres. The microspheres can be made to be small in size with a narrow range of particle size distribution and a high sphericity. In one aspect, the microspheres provided herein are provided in the form of spherical cores comprising maltodextrin or maltodextrin and starch and are prepared using a centrifugal tumbling-granulating-coating apparatus. In another aspect, the spherical cores can be powder-coated with one or more layers of small particles, such as starch particles. The microspheres provided herein can be used as cores for multi-particulate solid dosage delivery systems as well as other pharmaceutical, nutraceutical, food, personal care, and other applications.

15 Claims, 3 Drawing Sheets

(51) Int. Cl.
*A61K 9/50* (2006.01)
*A61K 9/16* (2006.01)

(56) References Cited

U.S. PATENT DOCUMENTS

| | | | |
|---|---|---|---|
| 4,695,323 A * | 9/1987 | Rueckl | 106/690 |
| 5,064,669 A * | 11/1991 | Tan et al. | 426/307 |
| 5,506,353 A * | 4/1996 | Subramaniam | 536/103 |
| 5,904,951 A | 5/1999 | Yamanaka et al. | |
| 6,468,568 B1 | 10/2002 | Leusner et al. | |
| 6,613,898 B1 | 9/2003 | Berresi et al. | |
| 6,745,960 B1 | 6/2004 | Myo et al. | |
| 6,919,446 B1 | 7/2005 | Antrim et al. | |
| 6,946,149 B2 | 9/2005 | Bazin et al. | |
| 7,018,651 B2 * | 3/2006 | Burger et al. | 424/464 |
| 7,091,335 B2 | 8/2006 | Antrim et al. | |
| 7,226,760 B2 | 6/2007 | Bazin et al. | |
| 7,405,293 B1 | 7/2008 | Barresi et al. | |
| 7,553,992 B2 * | 6/2009 | Oberegger et al. | 564/345 |
| 7,595,393 B2 | 9/2009 | Barresi et al. | |
| 7,726,591 B2 | 6/2010 | Basten | |
| 7,728,125 B2 | 6/2010 | Barresi et al. | |
| 7,753,298 B2 | 7/2010 | Basten | |
| 7,816,105 B2 | 10/2010 | Bazin et al. | |
| 7,943,171 B2 | 5/2011 | Serpelloni | |
| 2007/0036704 A1 | 2/2007 | Liu | |
| 2007/0071819 A1 * | 3/2007 | Kesarwani et al. | 424/468 |
| 2013/0004546 A1 | 1/2013 | Laugier | |
| 2013/0071479 A1 | 3/2013 | Freers et al. | |

FOREIGN PATENT DOCUMENTS

| | | |
|---|---|---|
| FR | 2778336 A1 | 11/1999 |
| FR | 2955258 A1 | 7/2011 |
| WO | WO 2004084863 A1 * | 10/2004 |

OTHER PUBLICATIONS

International Search Report and Written Opinion of the International Search Authority, dated Mar. 5, 2013.
International Search Report and Written Opinion for PCT/US2013/060674 dated Dec. 26, 2013 (32 pages).

* cited by examiner

MICROSPHERES

CROSS-REFERENCE TO RELATED APPLICATION

This application claims the benefit of earlier U.S. Provisional Patent Application Ser. No. 61/536,919, filed Sep. 20, 2011. The entire contents of the earlier provisional application are hereby incorporated by reference in its entirety.

FIELD

The disclosure relates in various aspects to microspheres, to processes for producing the microspheres, and to products incorporating the microspheres.

BACKGROUND

Microspheres composed of inert or comestible materials are used in various industries. In the pharmaceutical industry, for instance, such microspheres typically are used for applications such as solid dosage delivery systems with coatings for controlled release formulas. The microspheres, also called "nonpareils," can be used as the seed for drug layering and optional subsequent application of various coatings. The coated microspheres can then be incorporated into tablets, capsules, powders, suspensions or other dosage forms.

The use of microspheres in controlled release solid dosage forms is believed to allow the tablet, capsule or powder to release the active ingredient over time at a controlled rate. This dosage form in many embodiments is believed not only to insure an accurate dose, but also to distribute the dose throughout the gastrointestinal tract instead of in one location. This is understood to decrease an undesirable pharmacological effect known as "dose dumping" and related toxic effects from the active ingredient.

Commercially available microspheres include sugar-based microspheres, microcrystalline cellulose-based microspheres and some starch-based microspheres. Sugar microspheres typically include 90 to 95 percent sucrose and 5 to 10 percent starch as the binder. These microspheres are relatively cost effective, and are satisfactory in many applications. It can be difficult to prepare sugar microspheres having a particle size under 400 microns, however. Also, conventional techniques for preparing sugar-based microspheres can provide particle size distribution of the microspheres that is wider than desired. Sugar microspheres also can be reactive with certain active drug products and some nutraceutical ingredients, thereby causing a decrease in the overall stability of the dosage form. When employed in coated applications, sugar microspheres can become tacky and hinder drug layering during the coating process. Because the sugar is water soluble and can dissolve when it comes in contact with aqueous coatings, the sugar cores can become difficult to coat and can stick to each other and to the surface of the pan. Also, certain applications, such as use of microspheres in pharmaceutical products, require cores that are less soluble than sugar-based cores to prevent agglomeration during processing and for effective stability and dissolution.

Microspheres based on microcrystalline cellulose (MCC) can provide an inert core for drug layering and coating. MCC-based microspheres are relatively dense and most have a relatively smooth surface to allow for uniform dosage of the active ingredient being applied to the core. However, the particle size distribution of MCC-based microspheres often is not uniform. Also, MCC microspheres are cost prohibitive for many economical finished dosage formulations and can absorb moisture from the coating process, which is undesirable in many embodiments because moisture absorption can cause decreased stability of the finished dosage form.

Starch microsphere cores also are known. Presently, these cores are not readily available commercially and are not available in the small particle size desired by many finished product manufacturers. Both sugar-based and MCC-based microspheres are believed to exhibit a change in solubility profile over time. Some studies have shown the dissolution of a coated sugar core may decrease over time, thus reducing the dosage of the active ingredient being released while the dissolution of a coated MCC-based core may increase over time, increasing the amount of active ingredient being released.

SUMMARY

In some embodiments, substantially uniform, high density microspheres comprising maltodextrin or maltodextrin and starch are provided. In other embodiments, methods of making the microspheres are provided herein. In still other embodiments, the invention encompasses pharmaceutical products made with such microspheres, and in other embodiments, the invention encompasses methods for preparing pharmaceutical products.

In some embodiments, the microspheres provided herein are provided in the form of cores, the cores being generally spherical. In some embodiments, the spherical cores can be coated with one or more layers of small particles, such as starch particles. At least in some embodiments, the microspheres have high sphericity.

By one approach, the method includes a granulation stage to form substantially uniform, high density spherical cores. A powder mixture is spherically granulated using a centrifugal tumbling-granulating-coating apparatus, such as the GRANUREX® GXR Rotor Granulation device from Vector Corporation (Marion, Iowa). In one aspect, the powder mixture comprises at least about 80 percent maltodextrin. In another aspect, the powder mixture comprises about 2 to about 50 percent maltodextrin and about 50 to about 98 percent starch, in another aspect about 10 to about 45 percent maltodextrin and about 55 to about 90 percent starch, and in another aspect about 20 to about 40 percent maltodextrin and about 60 to about 80 percent starch. An aqueous liquid, such as water, can be used as the granulating medium.

When the powder mixture comprises maltodextrin and starch, the spherical cores have a mean particle size of about 75 microns to about 300 microns, in some cases about 85 microns to about 175 microns, in some embodiments about 90 microns to about 150 microns, and in some embodiments about 100 to about 125 microns. Generally, when the powder mixture comprises at least 80 percent maltodextrin, the resulting spherical cores are smaller than when the powder mixture includes at least about 50 percent starch. In this respect, the maltodextrin spherical cores have a mean particle size of about 20 to about 100 microns, in another aspect about 50 to about 100 microns, in another aspect about 75 to about 100 microns. The spherical cores can be used as is or further processed to increase the size of the microspheres.

Generally, the microspheres can be increased to a desired particle size by adding one or more layers to the spherical cores. When starch is applied, the layers of starch may be composed of small starch particles as depicted in the Figures herein. In some embodiments, the methods described herein can be used to provide microspheres having a particle size of about 200 to about 2000 microns. By this approach, the method includes a granulation stage as described above to provide spherical cores which are used as seeds for a powder layering process so that the particle size of the microspheres can be increased to a desired size.

The microspheres can be incorporated into tablets, granulations, capsules, powders, or used as is.

DETAILED DESCRIPTION

Figure 1:
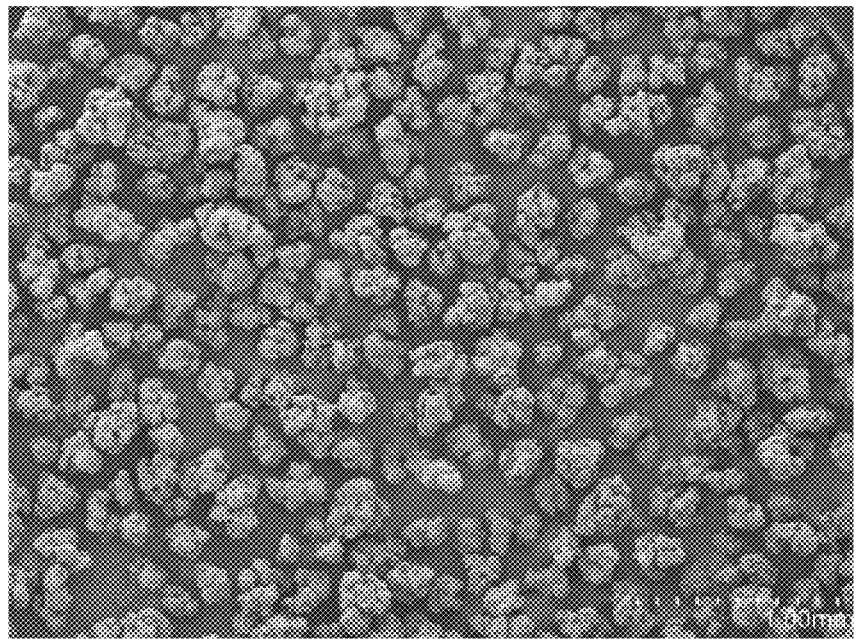
FIG. 1 is a scanning electron micrograph of maltodextrin and starch spherical cores prepared as described in Example 1.

As used herein, the term "microspheres" refers to spherical cores and specifically encompasses spherical cores either with or without one or more layers of small particles provided in a powder layering process.

Substantially uniform, high density microspheres and methods of making the microspheres are provided herein. In one aspect, the microspheres are provided in the form of spherical cores comprising maltodextrin. In another aspect, the microspheres are provided in the form of spherical cores comprising maltodextrin and starch. In another aspect, the spherical cores can be powder coated with one or more layers of small particles to increase the size of the microspheres. By some approaches, the one or more layers of small particles comprise starch particles. Advantageously, at least in certain embodiments, the microspheres provided herein are effective to solve many of the problems associated with traditional sugar or microcrystalline cellulose microspheres described above, including drug stability, uniformity, sphericity, particle size, and moisture retention. It is believed in many embodiments that the microspheres prepared as described herein can be prepared economically.

The microspheres described herein can be provided in a variety of sizes having a mean particle size in any range deemed suitable, and in many cases in the range of about 25 microns to about 2000 microns. In many cases, it is desirable to provide spherical cores sized at the lower end of the size range (e.g., a mean particle size of about 25 microns to about 200 microns) and additional layers of the small particles can be applied to the spherical cores to provide larger sized microspheres.

The methods described herein can be used to provide substantially uniform microspheres. As used herein, the term "substantially uniform" means that the microspheres produced according to the methods described herein have a narrow particle size distribution and have a high sphericity without the need for screening to adjust particle size (e.g., by fluidized bed separation or screen filtering), although such techniques can be used if desired. Sphericity ($\psi$) is a measure of the roundness of an object. Sphericity is the ratio of the surface area of a sphere (which has the same volume as the particle being compared) to the surface of the particle being tested. Sphericity can be calculated according to the following formula:

$$\Psi = \frac{\pi^{\frac{1}{3}}(6V_p)^{\frac{2}{3}}}{A_p},$$

where $V_p$ is the volume of the sphere and $A_p$ is the surface area of the sphere. By some approaches, the spherical cores produced in accordance with the disclosure have a sphericity value of at least about 0.6, in another aspect at least about 0.7, in another aspect at least about 0.8, and in yet another aspect at least about 0.9. For this disclosure, sphericity was measured by aspect ratio using a Sympatec, Inc. GMBH QICPIC with RODOS/L Dry Dispersing Module. The population of microspheres produced may include some microspheres having a lower sphericity value while providing the desired high sphericity value for the overall population of microspheres. Generally, coating the spherical cores with one or more layers of starch particles will increase the sphericity value of the microspheres. In one aspect, a population of coated spherical cores has a mean sphericity value of at least about 0.6, in another aspect at least about 0.7, in another aspect at least about 0.8, and in yet another aspect at least about 0.9.

In some embodiments, the methods described herein can be used to provide spherical cores having a mean particle size of about 20 to about 200 microns. In other embodiments, larger, more traditionally-sized microspheres (e.g., microspheres having a mean particle size of about 300 to about 2000 microns) can also be made. The size of the microspheres can be substantially controlled using techniques such as powder layering in one or more stages.

By one approach, the method may include a granulation stage to form substantially uniform, high density spherical cores. A powder mixture of starch and maltodextrin is spherically granulated using a centrifugal tumbling-granulating-coating apparatus, such as the GRANUREX® GXR Rotor Granulation device from Vector Corporation (Marion, Iowa) and the device described in U.S. Pat. No. 7,726,591 to Vector Corporation, which is incorporated herein by reference in its entirety.

In one aspect, the powder mixture comprises at least about 80 percent maltodextrin. In another aspect, the powder mixture comprises about 2 to about 50 percent maltodextrin and about 50 to about 98 percent starch, in another aspect about 10 to about 45 percent maltodextrin and about 55 to about 90 percent starch, and in another aspect about 20 to about 40 percent maltodextrin and about 60 to about 80 percent starch. An aqueous liquid, such as water, may be employed as the granulating medium, as may any other suitable liquid.

When the powder mixture comprises maltodextrin and starch, the spherical cores have a mean particle size of about 75 microns to about 300 microns, in another aspect about 85 microns to about 175 microns, in another aspect about 90 microns to about 150 microns, and in yet another aspect about 100 to about 125 microns. Generally, when the powder mixture comprises at least 80 percent maltodextrin, the resulting spherical cores are smaller than when the powder mixture includes at least about 50 percent starch. In this respect, the maltodextrin spherical cores have a mean particle size of about 20 to about 100 microns, in another aspect about 50 to about 100 microns, in another aspect about 75 to about 100 microns. The spherical cores can be used as is or further processed to increase the size of the microspheres.

Any suitable maltodextrin can be used in conjunction with the invention. The maltodextrin can be derived from corn or other suitable grain. Maltodextrins are generally linear malto-ologisaccharides having a dextrose equivalent value less than 20. In this disclosure, maltodextrins further are deemed to include reduced maltodextrins, which are similar carbohydrates but in which the reducing end group has been itself chemically reduced. The invention is particularly applicable to malto-oligosaccharide species in which at least a portion of the malto-oligosaccharides in the mixture have a DP value greater than 5. Preferably, at least one of the malto-oligosaccharide species in the mixture has a DP value of 8 or more. More preferably, at least one species has a DP value of at least 10. For example, in preferred embodiments of the invention, at least 80 percent of the malto-oligosaccharide species in the mixture have a DP greater than 5, and at least 60 percent may have a DP greater than 8. In another embodiment, at least 80 percent of the malto-oligosaccharides species have a DP greater than 10. In some embodiments of the invention, the DP profile of the starting mixture is such that at least 75 percent of the malto-oligosaccharides species in the mixture have a DP greater than 5 and at least 40 percent of the species in the mixture have a DP greater than 10. Such starting materials may be obtained conventionally, for example, by the partial hydrolysis of starch.

Further teachings concerning maltodextrins and malto-oligosaccharides more generally can be found in U.S. Pat. No. 7,728,125 ("Reduced malto-oligosaccharides"); U.S. Pat. No. 7,595,393 ("Reduced malto-oligosaccharides"); U.S. Pat. No. 7,405,293 ("Reduced malto-oligosaccharides"); U.S. Pat. No. 7,091,335 ("Derivatized reduced malto-oligosaccharides"); U.S. Pat. No. 6,919,446 ("Reduced malto-oligosaccharides"); and U.S. Pat. No. 6,613,898 ("Reduced malto-oligosaccharides"), all assigned to Grain Processing Corporation of Muscatine, Iowa.

Suitable malto-oligosaccharides are sold as maltodextrins under the trademark MALTRIN® by Grain Processing Corporation of Muscatine, Iowa. The MALTRIN® maltodextrins are malto-oligosaccharide products, each product having a known typical DP profile. MALTRIN® maltodextrins suitable as binders include, for example, MALTRIN® M040, MALTRIN® M100, MALTRIN® M150, and MALTRIN® M180. The low dextrose equivalence of maltodextrin is believed to enhance the stability of the spheres when active ingredients are applied to the surface. The maltodextrin used to prepare the microspheres has a low dextrose equivalence, such as DE value of less than 12. Inclusion of such maltodextrins can enhance the stability of active ingredients applied to the sphere surface. While not wishing to be limited by theory, it is believed that the microspheres provided herein have lower reactivity with active ingredients than sugar-based microspheres, thereby increasing the stability of the active ingredients.

Any suitable starch may be used in conjunction with the invention. The starch may be derived from corn, wheat, rice, potato, tapioca, or other suitable source. For example, the PURE-DENT® starches available from Grain Processing Corporation of Muscatine, Iowa may be employed.

In one aspect, a suitable starch is powdered PURE-DENT® B815 Corn Starch NF and a suitable maltodextrin is MALTRIN® M520 Maltodextrin NF from Grain Processing Corporation. In other embodiments, the starch is a partially hydrolyzed porous starch, such as PURE-DENT® B730 modified food starch, also from Grain Processing Corporation. The use of porous granular starch is believed to enhance the ability of the spheres to absorb other materials, such as bioactives. Further details concerning porous starches and their preparation can be found in U.S. Pat. No. 7,816,105 ("Method for preparing a fluid absorber"); U.S. Pat. No. 7,226,760 ("Method for preparing a fluid absorber"); and U.S. Pat. No. 6,946,148 ("Method for absorbing fluid"), all assigned to Grain Processing Corporation.

By another approach, the method may further include a layering process whereby larger microspheres can be produced. By this approach, the method includes a granulation stage as described above to provide microspheres which are used as seeds for a powder layering process so that the particle size of the microspheres can be increased to a desired size. In some embodiments, the powder layering process adds one or more layers of starch to the microspheres while using a maltodextrin solution to adhere the starch to the microspheres.

At least in certain embodiments, the microspheres described herein have good flowability due to the high sphericity values and have sufficient mechanical strength to withstand further processing in coating processes and/or tableting or capsule filling. The lower solubility of the microspheres described herein allow more efficient processing because they do not stick together to form agglomerates during processing.

The substantially uniform, high density microspheres described herein can advantageously be used in coatings, including multi-particulate coatings, aqueous film coatings, sugar coatings, as well as in other pharmaceutical, nutraceutical, food, personal care, and other applications. The microspheres can also be used in nutraceutical and food applications to deliver active ingredients, flavors, colors, sweeteners, artificial sweeteners, or other ingredients. These microspheres can be incorporated into tablets, granulations, capsules, powders, or used as is. These additives may be incorporated within the microspheres—either in the core or in the powder layering or both. They may contain an additional coating or they may be used without a coating. The coating may be a conventional coating or a controlled release coating. The ingredients added to the spheres may be used to enhance the properties of the spheres in a particular application, such as adding sweetness to spheres used in a chewable tablet or adding color to denote a particular drug product. The microspheres can also be used in nutraceutical and food applications to deliver active ingredients, flavors, colors, natural or artificial sweeteners, or other ingredients. For example, sweeteners useful in conjunction with the invention include but are not limited to sucralose, aspartame, stevia, honey, sucrose, and mixtures thereof, as well as other artificial or natural sweeteners.

By some approaches, the microspheres described herein can be used as cores for multi-particulate, solid dosage delivery systems. For example, the microspheres can be coated with active ingredients and then, if desired, coated with an enteric, delayed release, sustained release, or other type of coating. When the microspheres are used for drug delivery, at least in some approaches it may be advantageous that the surface of the microspheres be as smooth as possible to allow for a uniform layering of the drug or other active ingredient. Uniform layering of the active can result in a more accurate dose of active in the finished product.

The microspheres can also be used in food applications. For example, the microspheres can be used as sugar-free or low sugar sprinkles or powdered sugar substitutes for food products. If desired, the spheres may employ a colorant.

EXAMPLES

The following Examples are provided to illustrate certain embodiments of the invention, but should not be construed as limiting the invention in scope.

The following examples illustrate the use of starch and maltodextrin to create uniform, high density microspheres as well as the use of these microspheres as the core for drug layering are shown below.

Example 1

Spheres were manufactured on a GRANUREX® GXR Rotor Granulator from Vector Corporation (Marion, Iowa) equipped with an ATU Mini air atomized spray system. The process used a two-phase approach completed without discharging the bowl between steps.

Figure 2:
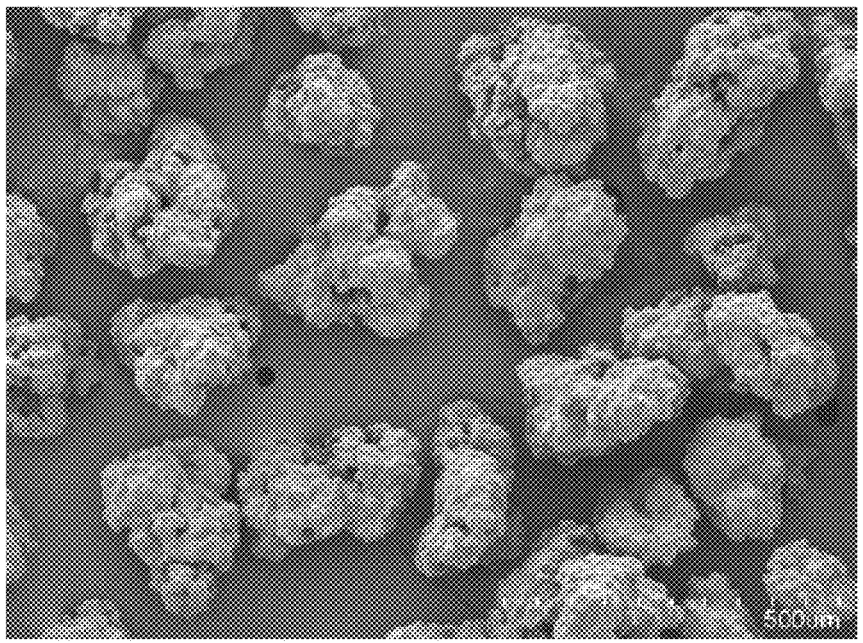
FIG. 2 is a scanning electron micrograph of maltodextrin and starch spherical cores prepared as described in Example 1.

In the first phase, the GRANUREX® bowl was initially charged with a powder blend of 70 percent (1400 grams) PURE-DENT® B815 Corn Starch NF and 30 percent (600 grams) MALTRIN® M520 Maltodextrin NF at a rotor speed of 400 rpm, slit air temperature set point of 50° C., slit air flow of 10 cubic ft./min (CFM), exhaust temperature of about 21° C., and solution pump speed of 14 rpm. Both excipients were fine particle size products (e.g., mean particle size of less than 75 microns) manufactured by Grain Processing Corporation. Using water as the granulating medium, the powder blend was spherically granulated and very small and uniform microspheres were prepared. 586 grams of water were applied in 45.5 minutes of spray time. The spherical granules were dried using a fluid bed air flow at 70 CFM, fluid bed air temperature set point of 70° C., exhaust temperature of about 24° C. to start and 28.4° C. when the seeds were dry. The product temperature was about 17° C. to start and 22.8° C. when the seeds were dry. The initial rotor granulation produced uniform, spherical granules with a mean diameter of 200 microns as shown in FIGS. 1 and 2.

In the second phase, the microspheres from the first phase were used as seeds for the powder layering process to create uniformly shaped microspheres of a larger size. Fine-powdered PURE-DENT® B815 Corn Starch NF was layered onto the seeds using the precision powder feeder and powder delivery system on the GXR Rotor Granulator. The corn starch was fed into the system at an initial rate of 20 grams/minute and then increased to 35 grams/minute. A 30 percent MALTRIN® M520 Maltodextrin NF in water solution was used to adhere the PURE-DENT® B815 Corn Starch NF powder. The maltodextrin was sprayed at an initial rate of 14 grams/minute and then increased to 17 grams/minute. The machine was set at a rotor speed of 200 rpm, slit air temperature set point of 50° C., slit air flow of 10 CFM, exhaust temperature of about 22° C., and pump speed of 16-19 rpm. The product temperature was about 17-20° C. A total of 1500 grams of PURE-DENT® B815 Corn Starch NF was applied using 908 grams of the 30 percent MALTRIN® M520 Maltodextrin NF solution.

Figure 3:
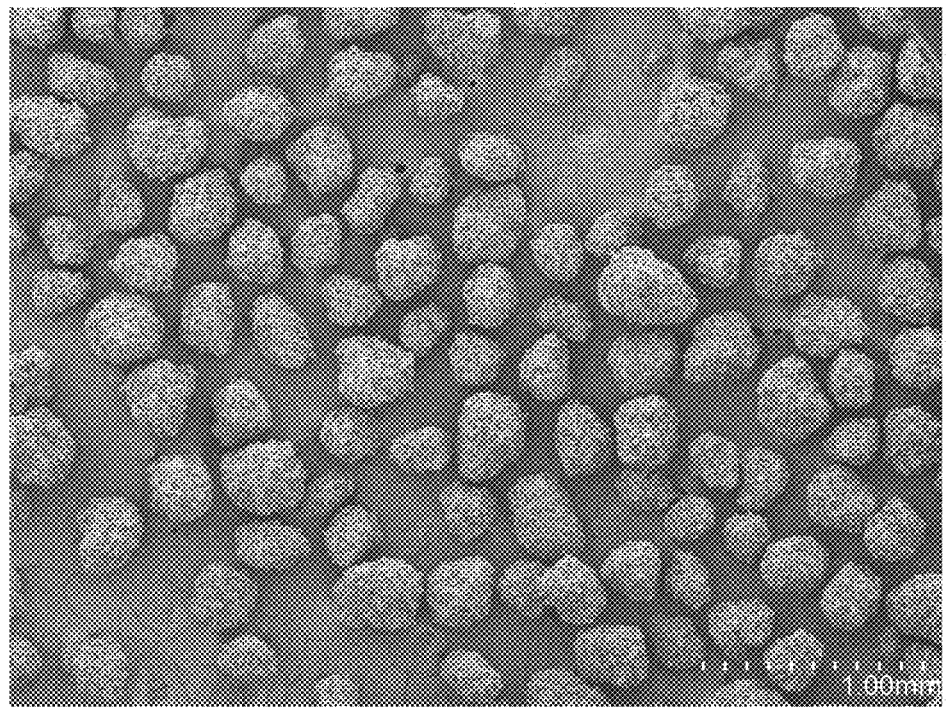
FIG. 3 is a scanning electron micrograph of powder-layered coated maltodextrin and starch spherical cores prepared as described in Example 1.
Figure 4:
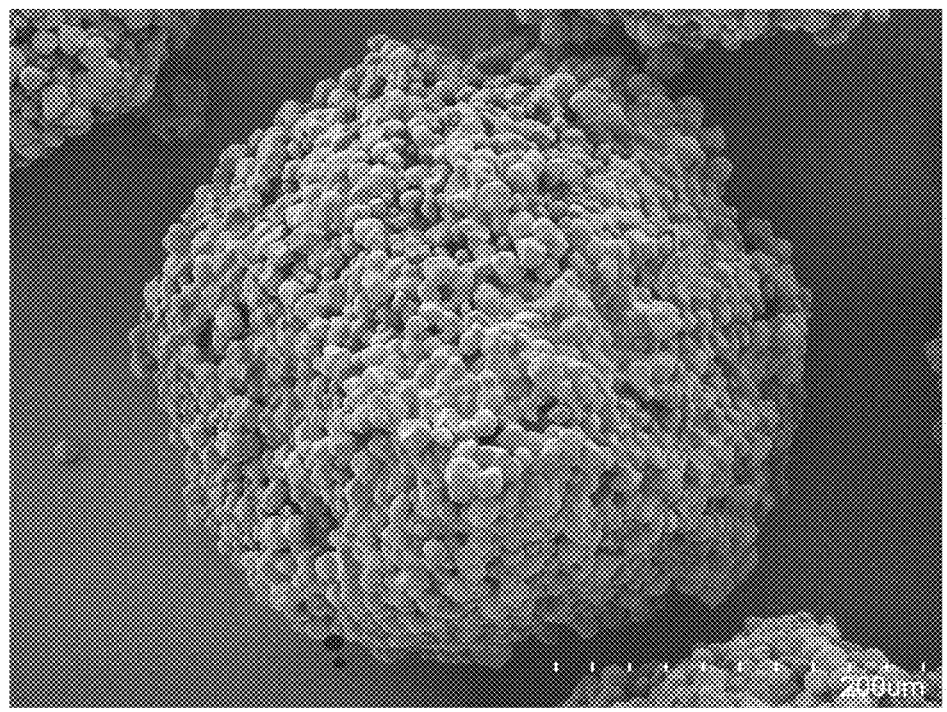
FIG. 4 is a scanning electron micrograph of powder-layered coated maltodextrin and starch spherical cores prepared as described in Example 1.

The spherical granules were dried using a fluid bed air flow at 70 CFM, fluid bed air temperature set point of 70° C., slit air flow of 20 CFM, rotor speed of 150 rpm, and exhaust temperature of about 22° C. The product temperature was about 17° C. The coated particles are shown in FIGS. 3 and 4.

The powder layering process increased the size of the microspheres to the desired 300-400 microns. The initial spheronizing and layering steps were completed in 90 minutes to build a 300-400 micron finished bead.

Example 2

This experiment compares the processing and results of using two different core materials, sugar/starch nonpareils and maltodextrin/starch microspheres, in a dry powder layering process using theophylline as the active drug ingredient.

Figure 5:
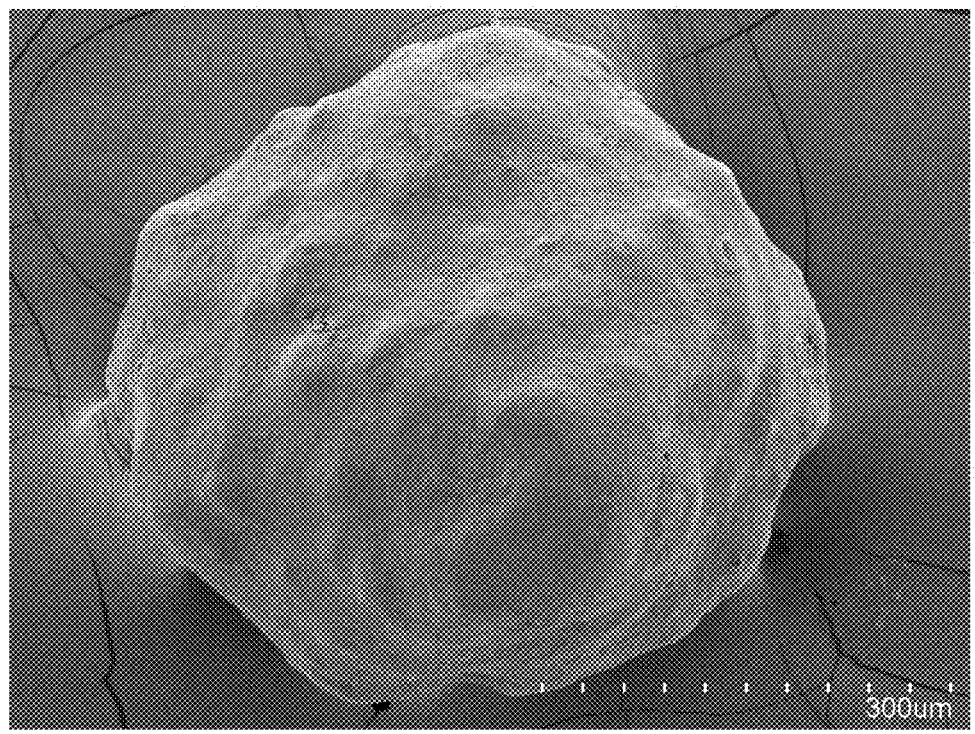
FIG. 5 is a scanning electron micrograph of a powder-layered coated maltodextrin and starch spherical core subsequently coated with a drug layer and then an enteric coating as described in Example 2.
Figure 6:
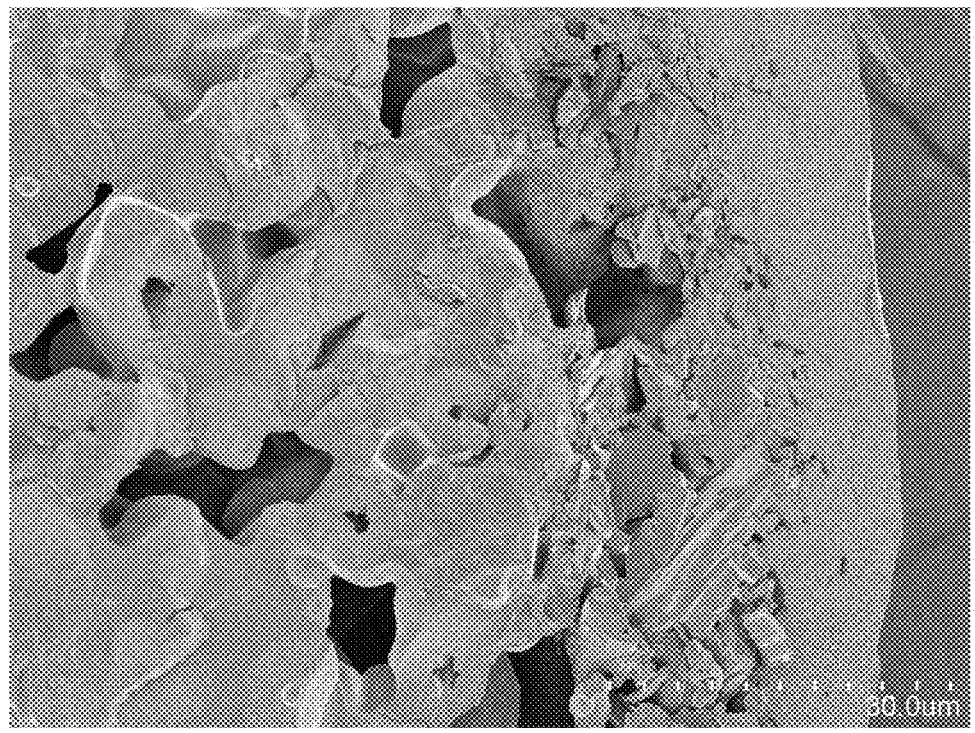
FIG. 6 is a scanning electron micrograph of a cross-sectional view of a powder-layered coated maltodextrin and starch spherical core subsequently coated with a drug layer and then an enteric coating as described in Example 2.

Initially, 3 kg of 40/50 mesh sugar/starch cores were loaded into a Vector GRANUREX® GXR-35 rotor granulator. Next, 529 g of micronized theophylline was loaded into a K-Tron KT-20 powder feeder and dry layered onto the microspheres, using a 5 percent KOLLIDON® K-30 polyvinylpyrrolidone (PVP) binding solution in water. The process was repeated utilizing maltodextrin/starch microspheres as the core material. Following the drug layering, each batch of drug layered microspheres were coated with a 20 percent coating of EUDRAGIT® L 30 D-55 enteric coating for enteric protection. Dissolution, size and shape analysis and SEM cross sections were done and combined with process data to compare the two core materials. The maltodextrin and starch spherical core coated with the drug layer and enteric coating are shown in FIGS. 5 and 6.

The results showed the theophylline was successfully applied to both types of core materials, but that the sugar/starch microspheres showed more of a tendency to become tacky and agglomerate during the drug layering step. The maltodextrin/starch microspheres did not show any sticking problems throughout the run. Both types of cores exhibited very high processing efficiencies, each having 97 percent processing yields. Dissolution testing showed nearly identical drug release from the two types of cores. Size analysis showed that the maltodextrin/starch microspheres were slightly more uniform in size following the drug layering, which is likely due to them being more uniform in size prior to processing.

The results of the testing showed that the maltodextrin/starch microspheres behaved very similarly to the sugar/starch cores in the dry powder layering process. The processes with both sets of cores had very efficient results and produced uniformly coated products. The dissolution testing showed that the release rates were nearly identical for both sets of cores. The maltodextrin/starch microspheres did provide some slight processing advantages in that they showed less tendency to agglomerate during the drug layering step. The testing showed that maltodextrin/starch microspheres could be used as a suitable replacement for sugar/starch cores.

Example 3

In this Example, PURE-DENT® B730 modified food starch was used with maltodextrin. The spheres in this example were manufactured to a final level of 70 percent starch and 30 percent maltodextrin. The spheres were manufactured on a GRANUREX® GXR Rotor Granulator (Freund-Vector Corporation) equipped with an ATU Mini air atomized spray system. Microsphere cores made of 70% PURE-DENT® B815 Corn Starch NF and 30% MALTRIN® M520 Maltodextrin NF (Grain Processing Corporation) were used as seeds for the powder layering process. PURE-DENT® B730 food starch-modified was layered onto the seeds using 30 percent MALTRIN® M100 Maltodextrin NF in water as the binding solution. The cores used as seeds had a mean diameter of 200 microns. The powder layering process increased the size of the spheres to approximately 400 microns.

Example 4

Spheres were manufactured to a final level of 30 percent by weight sucralose, 40 percent corn starch and 30 percent maltodextrin. The spheres were manufactured on a GRANUREX® GXR Rotor Granulator (Freund-Vector Corporation) equipped with an ATU Mini air atomized spray system. Microsphere cores made of 70% PURE-DENT® B815 Corn Starch NF and 30% MALTRIN® M520 Maltodextrin NF (Grain Processing Corporation) were used as seeds for the powder layering process. PURE-DENT® B810 Corn Starch NF blended with the sucralose was layered onto the seeds using 30 percent MALTRIN® M100 Maltodextrin NF in water as the binding solution. The cores used as seeds had a mean diameter of 200 microns. The powder layering process increased the size of the spheres to approximately 300 microns.

Example 5

This Example illustrates the compression properties of microspheres prepared in accordance with an embodiment of the invention.

Starch/maltodextrin spheres of various sizes were tested against commercial sugar spheres (SUGLETS® sugar microspheres, from Colorcon) and commercial microcrystalline cellulose spheres (CELPHERES, from Asahi Kasei). The spheres were fashioned into tablets with no other excipients. The tablets thus formed were compressed on a Colton Rotary Tablet Press equipped with 7/16 inch standard round tooling. Weight, hardness, friability, and disintegration properties were determined according to the following procedures:

Weight
1. Weigh three groups of 10 tablets to the nearest 0.001 grams on an analytical scale.
2. Average the weights recorded and express in mg or as grams per 10 tablets.

Hardness
1. Individually test the hardness of 10 tablets using the Dr. Schleuniger Pharmatron 8M tablet tester.
2. Tablet tester set up
    Turn hardness tester on.
    Select Automatic mode by using the Mode function in the Test Setup menu.
    Set sample size to 10 by using the Product Setup menu: Edit: Sample Size menu.
    Select kp for the unit of measure
3. Place tablet in testing area (pressing jaw) and run hardness test.
4. Clean the testing area after each tablet using a small paint brush.
5. Add second sample and repeat directions 3-5 until all 10 tablets are tested.
6. Press right arrow on front panel to view mean and record.

Friability
1. Provide 10 tablets and record weight in grams
2. Place tablets in the Roche drum of a Pharma Test Type PTF 1 friabulator and tumble for 4 minutes.
3. After tumbling, record weight (in grams) of the tablets. Calculate percent loss:

$$\frac{\text{Original weight of tablets} - \text{weight of tumbled tablets}}{\text{Original weight of tablets}} \times 100$$

Note: If a tablet broke, the tablet was deemed to fail the friability test.

Disintegration
Measure per USP Pharmacopeia method: General chapters: Physical Tests and Determination, <701> Disintegration The following results were obtained:

| Spheres Samples | Weight (mg) | Hardness (kp) | Friability (%) | Disintegration (min:Sec) |
|---|---|---|---|---|
| Example 5A: 200-300 μm spheres | 441 | 9.2 | 0.23 | 10:16 |
| Comparative Example 1: CELEPHERES 200-300 μm spheres | 517 | too soft | fail | 0:22 |
| Example 5B: 850-1000 μm spheres (1500 psi compression) | 414 | 1.4 | 1.06 | 5:45 |
| Example 5C: 850-1000 μm spheres (3500 psi compression) | 417 | 4.3 | 0.44 | 8:38 |
| Comparative Example 2: SUGLETTS® 850-1000 μm spheres | 541 | 2.6 | fail | 4:12 |

The starch/maltodextrin microspheres tableted very well with no sticking or die-wall friction on the press. The sugar spheres were much stickier than the starch/maltodextrin spheres which resulted in die-wall friction on the press. Also, the sugar spheres broke under pressure. The results showed the starch/maltodextrin spheres provided a harder tablet and the spheres maintained their integrity. Friability was better than the competitive spheres. Disintegration increased as the hardness of the tablet increased.

Example 6

Starch/maltodextrin spheres were tested against commercial sugar spheres and commercial microcrystalline cellulose spheres in combination with maltodextrin and starch, which are direct compression tableting excipients. The spheres were added at a 50% concentration in tablets comprised of 25% maltodextrin (MALTRIN® M100 maltodextrin from Grain Processing Corporation) and 25% pregelatinized corn starch (SPRESS® B820 Pregelatinized Corn Starch NF from Grain Processing Corporation) The tablets were compressed on a Colton Rotary Tablet Press equipped with 7/16 inch standard round tooling. The tablets were evaluated as per Example 5, yielding the following results:

| 50% spheres | Weight (mg) | Hardness (kp) | Friability (%) | Disintegration (min:Sec) |
|---|---|---|---|---|
| Example 6A: 200-300 μm spheres | 473 | 10.1 | 0.26 | 12:23 |
| Comparative Example 3: CELPHERES 200-300 μm | 495 | 4.7 | 0.27 | 14:35 |
| Example 6B: 850-1000 μm spheres | 495 | 8 | 0.2 | 11:22 |
| Comparative Example 4: SUGLETTS ® 850-1000 μm | 532 | 3.6 | 0.64 | 12:15 |

The starch/maltodextrin microspheres tableted very well with no sticking or die-wall friction on the press. The sugar spheres were stickier than the starch/maltodextrin spheres/ Also, the sugar spheres broke under pressure. The results showed the starch/maltodextrin spheres provided a harder tablet and the spheres maintained their integrity. Friability was better for the starch/maltodextrin spheres than the competitive sugar spheres and similar to the microcrystalline cellulose spheres. Disintegration was similar for all tablets.

It is thus seen that microspheres based on maltodextrin or on starch and maltodextrin may be provided.

The references cited herein are incorporated by reference in their entireties.

Uses of singular terms such as "a," "an," are intended to cover both the singular and the plural, unless otherwise indicated herein or clearly contradicted by context. The terms "comprising," "having," "including," and "containing" are to be construed as open-ended terms. All references, including publications, patent applications, and patents, cited herein are hereby incorporated by reference. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A microsphere composition comprising a plurality of microspheres each comprising a spherical core comprising maltodextrin, the plurality of microspheres having a mean particle size of about 20 to about 300 microns, wherein the spherical cores comprise a mixture of about 10 to about 45 percent maltodextrin and about 55 to about 90 percent starch.

2. The microsphere composition according to claim 1, wherein the plurality of microspheres have a mean sphericity of at least 0.6.

3. The microsphere composition according to claim 1, wherein the spherical cores have a mean particle size of about 75 to about 200 microns.

4. The microsphere composition according to claim 1, wherein the spherical cores have a mean particle size of about 85 to about 175 microns.

5. The microsphere composition according to claim 1, wherein the spherical cores have a mean particle size of about 90 to about 150 microns.

6. The microsphere composition comprising a plurality of microspheres each comprising a spherical core comprising maltodextrin according to claim 1, the spherical cores being coated with at least one layer, said layer comprising starch particles, the coated microspheres have a mean particle size of about 200 to about 2000 microns.

7. The microsphere composition according to claim 6, wherein the microspheres further comprise a coating selected from the group consisting of an enteric coating, a delayed release coating, and a sustained release coating.

8. The microsphere composition according to claim 6, wherein the plurality of microspheres have a mean sphericity of at least 0.6.

9. The microsphere composition according to claim 1, said microspheres comprising spherical cores coated with starch in a powder layering process.

10. The microsphere composition according to claim 1, said microspheres being coated with a drug layer and then an enteric coating.

11. The microsphere composition according to claim 1, said microspheres being coated with a drug or other active ingredient.

12. The microsphere composition according to claim 6, the coating including a maltodextrin adherent.

13. The microsphere composition according to claim 7, further comprising a maltodextrin adherent.

14. The microsphere composition according to claim 1, wherein the spherical cores comprise about 20 to 40 percent maltodextrin and 60 to 80 percent starch.

15. The microsphere composition according to claim 14, wherein the spherical cores comprise about 30 percent maltodextrin and 70 percent starch.

* * * * *